US012685862B2

(12) United States Patent (10) Patent No.: US 12,685,862 B2
Ukimura et al. (45) Date of Patent: Jul. 21, 2026

(54) URINARY INCONTINENCE TREATMENT DEVICE

(71) Applicant: Kyoto Prefectural Public University Corporation, Kyoto (JP)

(72) Inventors: Osamu Ukimura, Kyoto (JP); Yasuyuki Naito, Kyoto (JP)

(73) Assignee: Kyoto Prefectural Public University Corporation, Kyoto (JP)

( * ) Notice: Subject to any disclaimer, the term of this patent is extended or adjusted under 35 U.S.C. 154(b) by 295 days.

(21) Appl. No.: 18/284,086

(22) PCT Filed: Mar. 24, 2022

(86) PCT No.: PCT/JP2022/013841
§ 371 (c)(1),
(2) Date: Sep. 26, 2023

(87) PCT Pub. No.: WO2022/202963
PCT Pub. Date: Sep. 29, 2022

(65) Prior Publication Data
US 2024/0165407 A1 May 23, 2024

(30) Foreign Application Priority Data
Mar. 26, 2021 (JP) ................................. 2021-052616

(51) Int. Cl.
*A61N 1/36* (2006.01)
*A61N 1/04* (2006.01)
(52) U.S. Cl.
CPC ....... *A61N 1/36007* (2013.01); *A61N 1/0484* (2013.01); *A61N 1/36034* (2017.08)
(58) Field of Classification Search
CPC ............ A61N 1/36007; A61N 1/36034; A61N 1/0484

(Continued)

(56) References Cited

U.S. PATENT DOCUMENTS 4,977,906 A * 12/1990 Di Scipio ............... A61F 13/42
128/885
2017/0182320 A1 6/2017 Kolb et al.
2020/0001080 A1 1/2020 Naitoh

FOREIGN PATENT DOCUMENTS

JP H07-120346 A 5/1995
JP 2002-200178 A 7/2002
(Continued)

OTHER PUBLICATIONS

International Search Report dated May 17, 2022 in counterpart International Application No. PCT/JP2022/013841 w/English translation.

(Continued)

*Primary Examiner* — Nadia A Mahmood
(74) *Attorney, Agent, or Firm* — DLA Piper LLP (US)

(57) ABSTRACT

A urinary incontinence treatment device includes: a sensor for detecting urination; stimulation pads configured to apply a stimulus to a wearer; and a mechanical member including a stimulus generation unit for generating a signal for causing the stimulation pads to apply the stimulus to the wearer and a control unit for controlling the stimulus generation unit to generate the signal in response to urination detection by the sensor. The stimulation pads include a first pair of stimulation pads and a second pair of stimulation pads. The stimulus generation unit supplies electrical signals having different frequencies. The first pair of stimulation pads and the second pair of stimulation pads are arranged such that an electrical signal applied from the first pair of stimulation pads and an electrical signal applied from the second pair of stimulation pads intersect each other in the wearer's body and a resulting interference wave reaches the bladder.

10 Claims, 3 Drawing Sheets

(58) Field of Classification Search
USPC .......................................................... 607/40
See application file for complete search history.

(56) References Cited

FOREIGN PATENT DOCUMENTS

| | | | | |
|---|---|---|---|---|
| JP | 2020-22771 A | 2/2020 | | |
| WO | WO-2010096380 A1 * | 8/2010 | ............. | A61B 18/12 |
| WO | 2018/147447 A1 | 8/2018 | | |

OTHER PUBLICATIONS

Written Opinion dated May 17, 2022 in counterpart International Application No. PCT/JP2022/013841.

* cited by examiner

200

300

URINARY INCONTINENCE TREATMENT DEVICE

TECHNICAL FIELD

This disclosure relates to a urinary incontinence treatment device.

BACKGROUND

Electrical stimulation treatments such as a low-frequency treatment are known as methods for treating urinary incontinence (see JP 2002-200178 A, for example). In the low-frequency treatment, a patient is subjected to low-frequency stimulation when he/she is not urinating to stimulate afferents in the sacral region of the spinal cord, thereby inhibiting contraction of the detrusor muscle to increase the bladder capacity to store urine (the amount of urine excreted in one urination). Treatment devices that apply low-frequency stimulation are divided into the following types: a device that delivers low-frequency stimuli from the body surface; and a device configured to be implanted in the body of a patient and directly stimulate the sacral nerves. According to the device that delivers low-frequency stimuli from the body surface, stimulation targets are the bladder wall and the pelvic floor muscles. Thus, therapeutic effects are not stable, and treatment using such a device has not become established as a treatment method. On the other hand, although the device configured to be implanted in the body is effective in terms of capability of achieving direct nerve stimulation, there is a problem in that it requires a surgical procedure for placement, which is extremely invasive for the patient. Low-frequency stimulation using such treatment devices is usually performed about twice a day and at fixed times of day. However, since low-frequency stimulation is applied to a patient when the patient is not urinating, i.e., when the bladder is stable, it is difficult to obtain stable therapeutic effects.

In light of the foregoing, it could be helpful to provide a urinary incontinence treatment device that can be expected to bring about stable therapeutic effects by effectively stimulating the nerves that are deep inside the body and localized around the bladder, even though the device is minimally invasive.

SUMMARY

We thus provide a urinary incontinence treatment device including:

a sensor that detects urination;
stimulation pads configured to apply a stimulus to a wearer; and
a mechanical member including:
(i) a stimulus generation unit that generates a signal that causes the stimulation pads to apply the stimulus to the wearer; and
(ii) a controller for the stimulus generation unit to generate the signal in response to urination detection by the sensor,
wherein
the stimulation pads include a first pair of stimulation pads and a second pair of stimulation pads,
the stimulus generation unit supplies electrical signals having different frequencies to the first pair of stimulation pads and the second pair of stimulation pads, respectively, the first pair of stimulation pads and the second pair of stimulation pads are each a pair of electrode pads configured to apply an electrical stimulus to the wearer when being supplied with the electrical signal,
the frequencies of the electrical signals are set to 4,000 Hz to 4,300 Hz and a difference between the frequency set for the first pair of stimulation pads and the frequency set for the second pair of stimulation pads falls within 200 Hz to 300 Hz and 1 Hz to 10 Hz, and
the first pair of stimulation pads and the second pair of stimulation pads are arranged such that the electrical signal applied from the first pair of stimulation pads and the electrical signal applied from the second pair of stimulation pads intersect each other in the wearer's body and a resulting interference wave reaches the bladder.

It is preferable that the sensor, the stimulation pads, and the mechanical member are attachable to a diaper.

It is preferable that the device further includes a diaper, the sensor and the stimulation pads are provided in the diaper, and the mechanical member is connected the sensor and the stimulation pads.

It is preferable that at least one of the sensor or the stimulation pads are formed on the diaper by patterning a conductive material.

Another urinary incontinence treatment device is a urinary incontinence treatment device attachable to a diaper that includes a sensor that detects urination, including:

stimulation pads configured to apply a stimulus to a wearer; and
a mechanical member including:
(i) a stimulus generator that generates a signal causing the stimulation pads to apply the stimulus to the wearer;
(ii) a sensor element connecting part for connecting the sensor to the mechanical member; and
(iii) a controller connected to the sensor element connecting part controls the stimulus generation unit to generate the signal in response to urination detection by the sensor,
wherein
the stimulation pads include a first pair of stimulation pads and a second pair of stimulation pads,
the stimulus generation unit supplies electrical signals having different frequencies to the first pair of stimulation pads and the second pair of stimulation pads, respectively,
the first pair of stimulation pads and the second pair of stimulation pads are each a pair of electrode pads configured to apply an electrical stimulus to the wearer when being supplied with the electrical signal,
the frequencies of the electrical signals are set to 4,000 Hz to 4,300 Hz and that a difference between the frequency set for the first pair of stimulation pads and the frequency set for the second pair of stimulation pads falls within 200 Hz to 300 Hz and 1 Hz to 10 Hz, and
the first pair of stimulation pads and the second pair of stimulation pads are arranged such that the electrical signal applied from the first pair of stimulation pads and the electrical signal applied from the second pair of stimulation pads intersect each other in the wearer's body and a resulting interference wave reaches the bladder.

It is preferable that at least one of the sensor or the stimulation pads is formed on the diaper by patterning a conductive material.

Alternatively, still another urinary incontinence treatment device is a urinary incontinence treatment device connectable to a diaper that includes a sensor that detects urination and stimulation pads configured to apply a stimulus to a wearer, the stimulation pads being electrode pads configured to apply an electrical stimulus to the wearer when being supplied with an electrical signal and including a first pair of stimulation pads and a second pair of stimulation pads, and the first pair of stimulation pads and the second pair of stimulation pads being arranged such that an electrical signal applied from the first pair of stimulation pads and an electrical signal applied from the second pair of stimulation pads when the diaper is worn intersect each other in the wearer's body and a resulting interference wave reaches the bladder, the urinary incontinence treatment device comprising:

a mechanical member including:

(i) a stimulus generator that generates a signal causing the stimulation pads to apply the stimulus to the wearer;

(ii) a sensor element connecting part that connects the sensor to the mechanical member; and (iii) a control unit connected to the sensor element connecting part and controls the stimulus generation unit to generate the signal in response to urination detection by the sensor, wherein the stimulus generation unit supplies electrical signals having different frequencies to the first pair of stimulation pads and the second pair of stimulation pads, respectively, and the frequencies of the electrical signals are set to 4,000 Hz to 4,300 Hz and that a difference between the frequency set for the first pair of stimulation pads and the frequency set for the second pair of stimulation pads falls within 200 Hz to 300 Hz and 1 Hz to 10 Hz.

It is preferable that at least one of the sensor or the stimulation pads are formed on the diaper by patterning a conductive material.

It is preferable that the control unit includes a frequency adjustment section, which sets a frequency according to a pathological condition.

Also, it is preferable that the control unit includes a time adjustment section, which sets a stimulus application time according to a pathological condition.

Alternatively, it is preferable that the control unit includes a frequency adjustment section and a time adjustment section, which set a frequency and a stimulus application time, respectively, according to a pathological condition.

We thus provide a urinary incontinence treatment device that can be expected to bring about stable therapeutic effects by effectively stimulating the nerves that are deep inside the body and localized around the bladder, even though the device is minimally invasive.

REFERENCE SIGNS LIST

Figure 1:
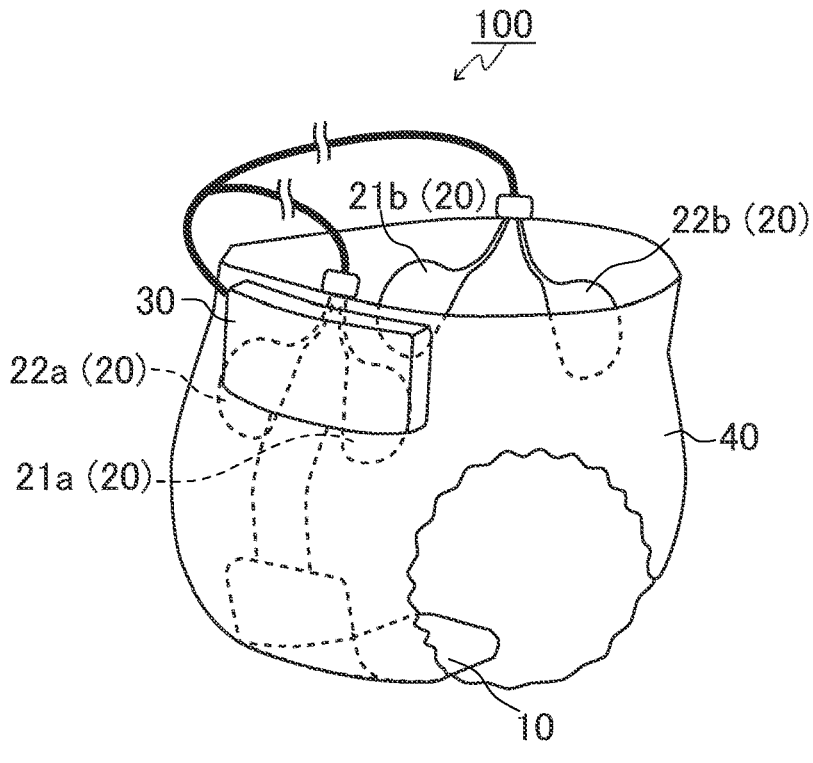
FIG. 1 schematically shows a urinary incontinence treatment device according to a first example.

100, 200, 300 Urinary incontinence treatment device
10, 10A, 10B Sensor
20, 20B Stimulation pad
21 First pair of stimulation pads (21a, 21b)
22 Second pair of stimulation pads (22a, 22b)
30, 30A, 30B Mechanical member
31 Stimulus generation unit
32 Control unit
33 Sensor element connecting part
40, 40A, 40B Diaper
P Bladder
Q Rectum
R Sacrum

DETAILED DESCRIPTION

In the following, our urinary incontinence treatment devices will be described with reference to illustrative examples. However, this disclosure is by no means limited to or restricted by the following examples. The drawings referred to in the following are all schematic representations, and the dimensional ratios and the like of objects depicted in these drawings may differ from the actual dimensional ratios and the like of the objects. Also, the dimensional ratios and the like may vary among the drawings.

First Example

Figure 2:
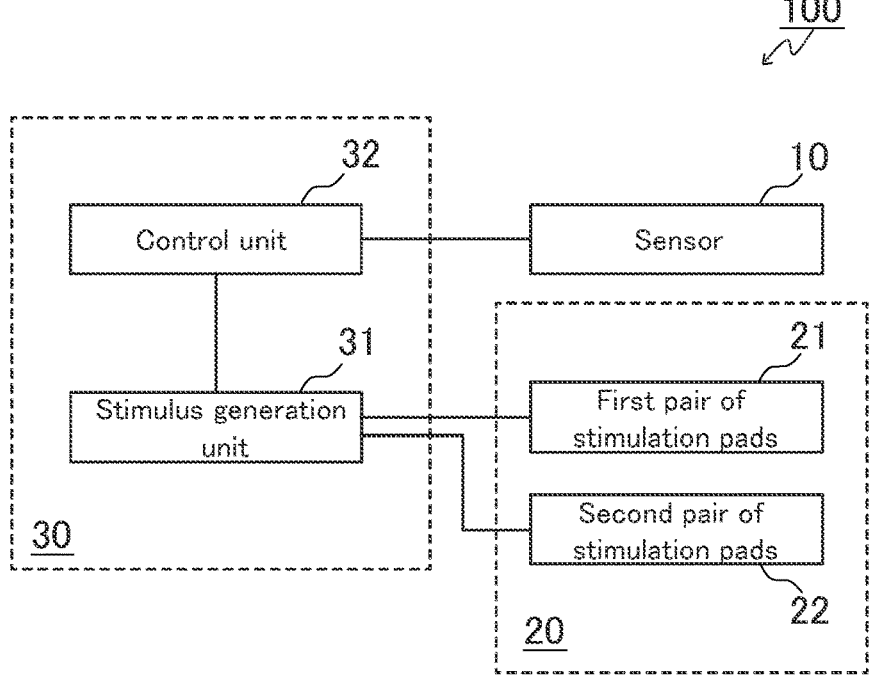
FIG. 2 is a block diagram showing an example of the structure of the urinary incontinence treatment device.

FIG. 1 schematically shows a urinary incontinence treatment device according to the first example. FIG. 2 is a block diagram showing an example of the structure of the urinary incontinence treatment device. A urinary incontinence treatment device 100 of the example includes a sensor 10, stimulation pads 20, and a mechanical member 30. The mechanical member 30 includes a stimulus generation unit 31 and a control unit 32. The sensor 10 detects urination. The sensor 10 is electrically connected to the control unit 32, which is included in the mechanical member 30. The stimulation pads 20 are configured to apply a stimulus to a wearer. The stimulation pads 20 are electrically connected to the stimulus generation unit 31, which is included in the mechanical member 30. The control unit 32 and the stimulus generation unit 31 are electrically connected to each other. The stimulus generation unit 31 generates signals causing the stimulation pads 20 to apply a stimulus to the wearer. The control unit 32 controls the stimulus generation unit 31 to generate the signal in response to urination detection by the sensor 10.

The stimulation pads 20 include a first pair 21 of stimulation pads and a second pair 22 of stimulation pads. The first pair 21 of stimulation pads (21a, 21b) and the second pair 22 of stimulation pads (22a, 22b) are each a pair of electrode pads configured to apply an electrical stimulus to the wearer when being supplied with an electrical signal.

The stimulus generation unit 31 supplies electrical signals having different frequencies to the first pair 21 of stimulation pads and the second pair 22 of stimulation pads, respectively. The frequencies of the electrical signals supplied to the first pair 21 of stimulation pads and the second pair 22 of stimulation pads are 4,000 Hz to 4,300 Hz. The frequencies of the electrical signals supplied to the respective stimulation pads are set such that, with the frequencies falling within the above-described range, the difference between the frequency set for the first pair of stimulation pads and the frequency set for the second pair of stimulation pads falls within 200 Hz to 300 Hz and 1 Hz to 10 Hz.

The first pair 21 of stimulation pads and the second pair 22 of stimulation pads are arranged such that the electrical signal applied from the first pair 21 of stimulation pads and the electrical signal applied from the second pair 22 of stimulation pads intersect each other in the vicinity of the bladder in the wearer's body. In a region where the electrical signals intersect each other, an interference wave having a frequency corresponding to the difference (phase difference) between the frequency of the electrical signal applied from the first pair 21 of stimulation pads and the frequency of the electrical signal applied from the second pair 22 of stimulation pads is generated.

The significance of setting the frequencies of the interference wave in 200 Hz to 300 Hz and 1 Hz to 10 Hz will be described.

The nerves of the bladder extend from the sacral spinal segments S2 to S4 to the urethra via the bladder smooth muscle and the bladder epithelium, and it is known that their nerve fibers consist of myelinated Aδ-fibers and unmyelinated C-fibers. Myelinated nerves (myelinated Aδ-fibers) are characterized by high nerve conduction velocities and transmit normal sensory information, and in the bladder, these nerve fibers transmit normal urges to urinate. Unmyelinated nerves (unmyelinated C-fibers) exhibit lower nerve conduction velocities than the myelinated nerves and transmit pathological sensory information, and in the bladder, these nerves transmit pathological urges to urinate, pain and the like.

Considering the mechanism of urinary incontinence, it is known that the urinary incontinence is caused by a complex combination of both the sensory nerves involved in perception of normal urges to urinate and the sensory nerves involved in perception of pathological urges to urinate. We focused on a diagnostic approach to investigate the cause of urinary incontinence utilizing the fact that the frequency that specifically stimulates the unmyelinated sensory nerves (unmyelinated C-fibers) of the bladder is 5 Hz and the frequency that specifically stimulates the myelinated sensory nerves (myelinated Aδ-fibers) of the bladder is 250 Hz. Then, we had the idea of stimulating nerve fibers localized around the bladder at a nerve fiber-specific frequency according to the pathological condition of each patient, thereby addressing the problem of unstable therapeutic effects. We further attempted to improve and stabilize the therapeutic effects by applying a low-frequency stimulus at a timing when spontaneous contraction of the bladder (involuntary urination by the patient) occurs and, to this end, they achieved the urinary incontinence treatment devices described herein.

Low-frequency treatment devices typically use low-frequency currents of 1 Hz to 1,200 Hz, which cause tingling sensations. Further, it is more difficult for low-frequency currents to reach portions deep inside the body than it is for high-frequency currents. With consideration given to the above, the urinary incontinence treatment device 100 is configured to apply electrical signals having different frequencies that are in a relatively high frequency region of 4,000 Hz to 4,300 Hz from two directions, namely, from a position where the first pair 21 of stimulation pads are arranged and from a position where the second pair 22 of stimulation pads are arranged, thereby causing an interference wave to be generated in an intersecting region of these two directions, and this allows a low-frequency stimulus to be effectively applied to a target site deep inside the body (nerve fibers localized around the bladder). This device does not require any surgical procedure such as implantation in the body, for placement, and thus is minimally invasive and places little burden on a patient. Nevertheless, the device can deliver an electrical stimulus having a specific frequency expected to bring about therapeutic effects to a portion deep inside the body.

The interference wave has a frequency corresponding to the difference (phase difference) between the two applied frequencies. Thus, the difference between the frequency of the electrical signal applied from the first pair of stimulation pads and the frequency of the electrical signal applied from the second pair of stimulation pads is set to 200 Hz to 300 Hz centered on 250 Hz, which is the frequency that specifically stimulates the myelinated sensory nerves (myelinated Aδ-fibers) of the bladder and 1 Hz to 10 Hz centered on 5 Hz, which is the frequency that specifically stimulates the unmyelinated sensory nerves (unmyelinated C-fibers) of the bladder. In general, the frequency that specifically stimulates nerve fibers varies depending on the diameter of the nerve fibers and thus varies among individuals. In addition, in myelinated nerves, the length and the spacing of myelin sheaths vary among individuals, and the frequency that specifically stimulates the nerve fibers also varies depending on the length and the spacing of the myelin sheaths. Therefore, taking these individual differences into consideration, the frequency of the interference wave is set in a somewhat broader frequency ranges respectively centered on 250 Hz and 5 Hz.

Sensor

The sensor 10 is not particularly limited as long as it can detect urination. The sensor 10 can detect urination by detecting a wet state. However, this disclosure is not limited thereto. Detection of the wet state can be achieved by monitoring an electrical property (physical property value) that changes in accordance with the wet state and detecting wetting based on the change in electrical property. The physical property value may be the resistance, conductance, impedance, capacitance or the like. A specific example of the structure of the sensor 10 is a sensor including: a sensor element provided with one pair of conductors arranged spaced apart from each other; and a detection circuit electrically connected to each of the conductors.

The sensor 10 can detect urination based on the difference in electrical property between when urine (water) is not present and when urine (water) is present in a detection region of the sensor (e.g., a region between the pair of conductors). Such a difference in electrical property is caused based on the fact that urine (water) is conductive.

For example, in urination detection based on the electric resistance, the electrical resistance is relatively high when the detection region is dry in the absence of urine (water), and the electric resistance decreases when the detection region is wetted owing to urination. In urination detection based on conductance, the conductance, which is the reciprocal of electric resistance, is relatively low when the detection region is dry in the absence of urine (water), and the conductance increases when the detection region is wetted owing to urination.

In one example, the sensor element is separable and electrically connected to a sensor connection site. The separable sensor element may be provided in a diaper to be described below. In this example, the sensor element may be formed directly on the diaper using a conductive resin or the like by a method such as printing to be described below.

In the urinary incontinence treatment device 100, it is preferable that the sensor element of the sensor 10 is configured to be arranged at or near a urine receiving portion.

Stimulation Pad

The stimulation pads 20 are electrode pads configured to apply an electrical stimulus to the wearer when being supplied with the electrical signal. The electrode pads 20 may have a structure similar to those of electrode pads used in electrical treatment devices for performing known low-frequency treatments and the like. In one example, the stimulation pads 20 may each be an electrode pad in which an electrode element and a gel part to be adhered to the body surface of a wearer are formed integrally. The gel part is preferably made of a material having adhesiveness and electrical conductivity (e.g., a water-containing urethane gel and a water-containing acrylic gel). Alternatively, as described below, thin electrode pads can be formed by a method such as printing using a conductive resin or the like.

The stimulation pads are configured to be electrically connected to the mechanical member 30 to be described below via, for example, a lead wire (cable), whereby they can receive electrical signals supplied from the mechanical member 30 and can supply the electrical signals to portions of the body to which the stimulation pads are adhered. Alternatively, the stimulation pads can be wirelessly connected to the mechanical member 30.

The stimulation pads 20 of this example include the first pair 21 of stimulation pads (21a, 21b) and the second pair 22 of stimulation pads (22a, 22b). There may be three or more pairs of stimulation pads. In each of the first pair 21 of stimulation pads and the second pair 22 of stimulation pads, an electrical signal having a predetermined frequency is generated between the stimulation pads forming the pair.

The first pair 21 of stimulation pads and the second pair 22 of stimulation pads are arranged such that the electrical signal applied from the first pair 21 of stimulation pads and the electrical signal applied from the second pair 22 of stimulation pads intersect each other in the wearer's body. Electrical signals with different frequencies are supplied by the respective pairs of stimulation pads to the wearer from different directions and intersect each other in the vicinity of a region where there are a group of nerves localized around and controlling the bladder, whereby a stimulus with a desired frequency can be applied to the region.

Figure 3:
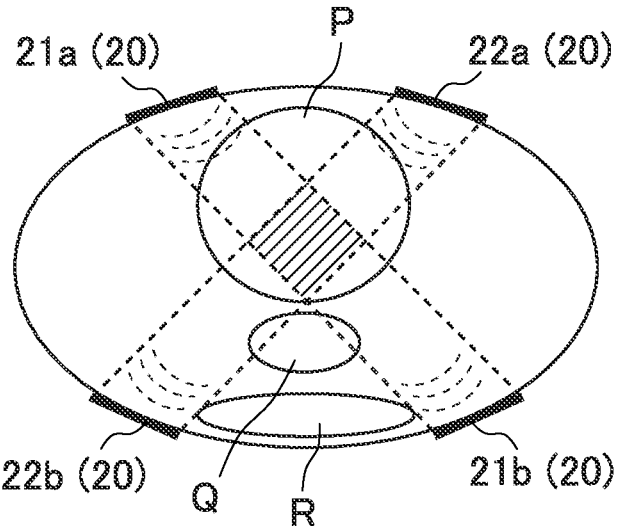
FIG. 3 schematically shows an example of the arrangement of stimulation pads of the urinary incontinence treatment device.

FIG. 3 schematically shows an example of the arrangement of the stimulation pads of the urinary incontinence treatment device. FIG. 3 illustrates the positional relation of the stimulation pads relative to the bladder P, the rectum Q, and the sacrum R with reference to a horizontal cross-sectional view of a region in the vicinity of the sacrum of the body. In FIG. 3, the upper side is the ventral side of the body and the lower side is the dorsal side of the body. The bladder P is located in the midline of the pelvic cavity, and the group of nerves that control the bladder P are concentrated in the dorsal side of the lower hemisphere of the bladder P. Thus, the region where the electrical signals from the respective pairs of stimulation pads intersect each other is preferably a region in the vicinity of the midline, which is indicated with oblique lines in FIG. 3. A specific example of the arrangement of the stimulation pads may be such that, at a height near a portion directly above the sacrum, the stimulation pad 21a forming the first pair 21 is on the left on the ventral side, the stimulation pad 21b forming the first pair 21 is on the right on the dorsal side, the stimulation pad 22a forming the second pair 22 is on the right on the ventral side, and the stimulation pad 22b forming the second pair 22 is on the left on the dorsal side. The arrangement of the stimulation pads is not limited to the above arrangement as long as they are arranged such that the electrical signals applied by the plurality of pairs of stimulation pads intersect each other in the wearer's body and a resulting interference wave reaches the bladder.

When three pairs of stimulation pads (not shown) are provided, they may be configured as follows. The frequencies of electrical signals applied by the respective pairs of stimulation pads are set as follows, for example: around 4,000 Hz for the first pair of stimulation pads; around 4,250 Hz for the second pair of stimulation pads; and around 4,005 Hz for the third stimulation pad pair. The respective pairs of stimulation pads are arranged such that a position at which the electrical signal applied from the first pair of stimulation pads and the electrical signal applied from the second pair of stimulation pads intersect each other and a position at which the electrical signal applied from the first pair of stimulation pads and the electrical signal applied from the third pair of stimulation pads intersect each other are in the vicinity of the bladder in the wearer's body. When a stimulus centered on a frequency of 250 Hz, which specifically stimulates the myelinated sensory nerves (myelinated Aδ-fibers) of the bladder, is to be applied, an interference wave is generated by applying electrical signals from the first pair of stimulation pads and the second pair of stimulation pads. On the other hand, when a stimulus centered on a frequency of 5 Hz, which specifically stimulates the unmyelinated sensory nerves (unmyelinated C-fibers) of the bladder, is to be applied, an interference wave is generated by applying electrical signals from the first and third pairs of stimulation pads. In this manner, it is also possible to obtain a desired frequency by determining the frequencies of electrical signals applied from the respective pairs of stimulus pads in advance and selecting the combination of the pairs of stimulus pads to be used, instead of adjusting the frequencies.

Mechanical Member

The mechanical member 30 includes the stimulus generation unit 31 that generates signals causing the stimulation pads 20 to apply a stimulus to the wearer and the control unit 32 causing the stimulus generation unit 31 to generate a stimulus in response to urination detection by the sensor 10. The main function of the mechanical member 30 is to generate a stimulus when urination is detected by the sensor 10 to cause the stimulation pads 20 to apply a stimulus to the wearer. The stimulus generation unit 31 and the control unit 32 can be implemented in a hardware manner by, for example, using a logic circuit formed on an integrated circuit (IC) chip. Alternatively, the stimulus generation unit 31 and the control unit 32 may be implemented in a software manner. In this example, the mechanical member 30 includes a CPU for executing program instructions, a memory for the CPU to run the program, an auxiliary storage device for storing the program and various data and the like, and the stimulus generation unit 31 and the control unit 32 are implemented when the CPU executes the program.

In the urinary incontinence treatment device 100, it is preferable that the mechanical member 30 is configured to be arranged at the abdomen. The mechanical member 30 may be arranged on the back side. However, considering when the device is worn while the wearer is lying down such as, for example, when the wearer is sleeping or in hospital, it is preferable that the mechanical member 30 is arranged at the abdomen because unpleasant sensations on the back of the wearer are reduced, and in addition, the mechanical member 30 can be attached and detached more easily.

Although FIG. 1 illustrates an example in which the stimulation pads 20 are connected to the mechanical member 30 (the stimulus generation unit 31) via a cable, this disclosure is not limited thereto. The stimulation pads 20 and the mechanical member 30 need only be electrically connected to each other, and they may be connected wirelessly, for example. Also, the connection is preferably switchable between wireless connection and wired connection. In a wireless connection, controlling the mechanical member 30 placed at the bedside when the wearer goes to bed is preferable from the viewpoint of providing the wearer with a good sleep, because unpleasant sensations caused by the mechanical member are eliminated.

Stimulus Generation Unit

The stimulus generation unit 31 is an electrical signal generation unit. The electrical signal generation unit generates electrical signals (AC voltage signals and AC current signals) having predetermined frequencies using a power source as a source of electrical power under the control of the control unit 32, and supplies the electrical signals to electrode elements of the electrode pads 20 (the first pair 21 of stimulation pads and the second pair 22 of stimulation pad).

The frequencies of the electrical signals are set as appropriate to 4,000 Hz to 4,300 Hz. At this time, the frequency (first frequency) of the electrical signal supplied to the first pair 21 of stimulation pads and the frequency (second frequency) of the electrical signal supplied to the second pair 22 of stimulation pads need to be different from each other, as described above. The frequencies of the electrical signals supplied to the respective pairs of stimulation pads are, for example, set in advance or input via a frequency input means to be described below, which may be included in the control unit 32. In both instances, they are set or input such that the difference between the first frequency and the second frequency is 200 Hz to 300 Hz and 1 Hz to 10 Hz. From the viewpoint of simplifying the urinary incontinence treatment device 100, the frequencies are preferably set in advance.

The output current and the output voltage can be set as appropriate within a range that does not compromise our desired effect. For example, the output current may be about 1 to 100 mA, preferably about 1 to 50 mA, and more preferably about 5 to 30 mA. The output voltage may be about 1 to 100 V, preferably about 2 to 80 V, and more preferably about 5 to 60 V. From the viewpoint of simplifying the urinary incontinence treatment device 100, the output current and the output voltage are preferably set in advance.

Control Unit

The control unit 32 is electrically connected to the sensor 10 and the stimulus generation unit 31, and causes the stimulus generation unit 31 to generate signals that causes the stimulus pads 20 (the first pair 21 of stimulation pads and the second pair 22 of stimulation pads) to apply a stimulus to the wearer in response to urination detection by the sensor 10. More specifically, when the sensor 10 detects urination (wet state) equal to or more than a predetermined threshold value, the control unit 32 sends to the stimulus generation unit 31 a control signal causing the stimulus generation unit 31 to generate electrical signals for a predetermined period of time.

The time for generating the electrical signals can be set as appropriate within a range that does not compromise our desired effect. For example, the time for generating the electrical signals may be about 10 seconds to 30 minutes, preferably about 5 to 20 minutes, and particularly preferably about 15 minutes. For example, the time for generating the electrical signals may be set in advance or may be input via a time input means to be described below, which may be included in the control unit 32. From the viewpoint of simplifying the urinary incontinence treatment device 100, the time for generating the electrical signals is preferably set in advance.

The control unit 32 can further include the following means:

a frequency input means that inputs a frequency of an electrical signal (making it possible to set a frequency for each patient);

a frequency adjustment section that adjusts a frequency to the frequency input via the frequency input means;

a time input means that inputs a time for generating electrical signals (making it possible to set a stimulus application time for each patient);

a time adjustment section that adjusts a stimulus application time to the time input via the time input means;

a switch that sends to the electrical signal generation unit, a control signal forcibly causing the electrical signal generation unit to generate electrical signals, regardless of the presence or absence of the detection by the sensor (forced generation switch); and a switch that forcibly stops sending of a control signal causing the generation of electrical signals, regardless of the presence or absence of the detection by the sensor (forced stop switch).

The frequency input means and the time input means may be configured such that values are directly input thereto, or they may be a component like a selection switch with which switching and selection from among a plurality of options are possible. Alternatively, a selection switch in which a plurality of patterns of the combination of frequency and time are set according to applicable pathological conditions and the type of treatment may be provided, and the frequency adjustment section and the time adjustment section may be controlled in accordance with the values corresponding to the selected pattern. The patterns may be set in advance, and it is more preferable if storing and setting of new patterns are also possible. Although the above description illustrates an example where the frequency adjustment section and the time adjustment section are included in the control unit 32 and the frequency and the stimulus application time are set according to the pathological condition, this disclosure is not limited thereto. The control unit 32 may include either one of the frequency adjustment section and the time adjustment section and may set the frequency or the stimulus application time according to the pathological condition.

Diaper

In a preferred example, the sensor 10, the stimulation pads 20, and the mechanical member 30 are attachable to a diaper 40. Alternatively, they may be attachable to undergarments worn at the crotch such as incontinence underpants, instead of the diaper 40. It is also preferable that the sensor 10 and the stimulation pads 20 attachable to the diaper 40 are provided in the diaper and the mechanical member 30 is electrically connected in a wireless manner or via other means.

The term "diaper" refers to an absorbent article worn at the crotch of a wearer to absorb and retain liquids such as urine. The diaper 40 is usually disposable.

The structure of the diaper 40 is known. It is usually composed of exterior body parts that serve as a front body part and a back body part when worn, and an absorber held between the front body part and the back body part in a cross-linked state. When the diaper 40 is worn, the water absorber is located at the crotch of a wearer and absorbs and retains liquids such as urine excreted from the wearer. The water absorber includes a water-absorbing material such as a superabsorbent polymer.

The diaper 40 may be for children (including infants, toddlers, and school children, and in particular, for grade school children (about 6 to 12 years old)), or may be for adults.

When the diaper 40 is for children, the urinary incontinence treatment device is suitably used to treat pediatric patients with nocturnal enuresis. In use of the urinary incontinence treatment device, it is not necessary for an adult to wake the patient up, and this greatly reduces the burden on both the adult and the patient compared to conventional alarm therapy.

When the diaper 40 is for adults, the urinary incontinence treatment device is suitably used to treat patients with urinary incontinence (including daytime urinary incontinence), particularly elderly patients. Treatment with the use of the urinary incontinence treatment device can reduce the frequency of occurrence of urinary incontinence to allow the patient to avoid or reduce the need to wear a diaper. This can prevent the patient's motivation from decreasing and dementia from progressing, for example. Furthermore, the reduction in the frequency of occurrence of urinary incontinence greatly reduces the burden on caregivers.

The urinary incontinence treatment device preferably further includes waterproof members for protecting the stimulation pads 20 from excreted urine. This prevents soiling of the stimulation pads 20 even when the back side of the wearer of the diaper 40 is wet due to a large amount of urination or for other reasons. With the stimulation pads 21*a* and 22*a* provided on the ventral side regarded as forming a pair and the stimulation pads 21*b* and 22*b* provided on the dorsal side regarded as forming another pair, there may be two waterproof members formed in a sheet-like shape entirely covering the stimulation pads of the respective pairs, and they may be arranged on the front side and the back side. However, the waterproof members are not limited to this example. For example, there may be four waterproof members covering each of the stimulation pads 21*a*, 21*b*, 22*a*, and 22*b* included in the first pair 21 and the second pair 22.

Second Example

Figure 4:
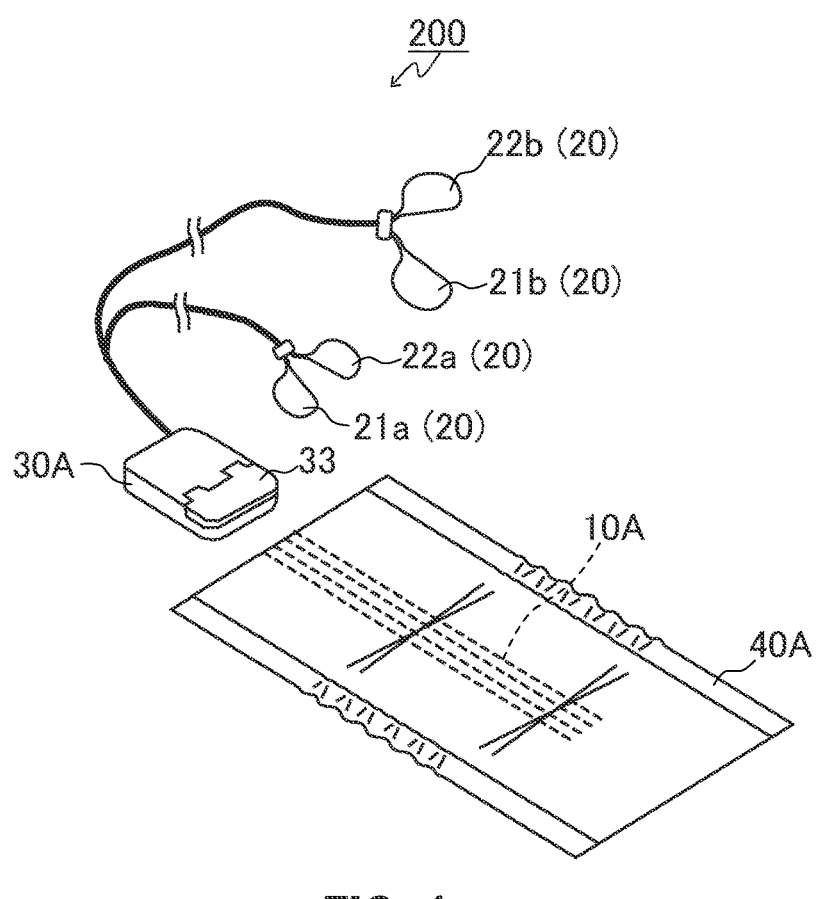
FIG. 4 schematically shows a urinary incontinence treatment device according to a second example.

FIG. 4 schematically shows a urinary incontinence treatment device according to the second example. The urinary incontinence treatment device 200 of this example is connectable to a diaper 40A provided with a sensor 10A for detecting urination, and includes stimulation pads 20 and a mechanical member 30A. One example of the diaper 40A provided with the sensor 10A is a training pad included in a nocturnal enuresis training system "Pisscall" manufactured by Awaji-Tec Co., Ltd. The urinary incontinence treatment device can be used in combination with such a diaper provided with a sensor. By attaching the mechanical member 30A (reusable) to the disposable diaper 40A provided with the sensor 10A, the daily use of the urinary incontinence treatment device is simplified. The sensor 10A may be formed directly on the diaper using a conductive resin or the like by a method such as printing to be described below.

In the urinary incontinence treatment device 200, the mechanical member 30A includes a stimulus generation unit 31 and a control unit 32, and further includes a sensor element connecting part 33 for connecting the sensor 10A to the mechanical member 30A. The mechanical member 30A is the same as the mechanical member 30 in the first example except that it further includes the sensor element connecting part 33.

The sensor 10 provided in the diaper 40A is connected to the sensor element connecting part 33 of the mechanical member 30A, whereby it is electrically connected to the control unit 32 included in the mechanical member 30A. When the sensor 10A detects urination, the detection of urination is transmitted to the control unit 32 via the sensor element connecting part 33. The control unit 32 and the stimulus generation unit 31 are electrically connected to each other. The stimulus generation unit 31 generates signals causing the stimulation pads 20 to apply a stimulus to the wearer. The control unit 32 controls the stimulus generation unit 31 to generate the signal in response to urination detection by the sensor 10A.

The sensor 10A shown in FIG. 4 includes a pair of strip-shaped conductors, and one end of each conductor extends to an end of the diaper 40. The sensor 10A can detect urination based on the difference in electrical property between when urine (water) is not present and when urine (water) is present in a region between these conductors. The sensor element connecting part 33 has a clip-like shape, and can hold the one ends of the conductors together with the diaper 40A. In this manner, the sensor element connecting part 33 connects the sensor 10A to the mechanical member 30A.

Although FIG. 4 illustrates an example in which the stimulation pads 20 are connected to the mechanical member 30A (the stimulus generation unit 31) via a cable as in the first example, this example is not limited thereto. Also, in this example, the stimulation pads 20 and the mechanical member 30 need only be electrically connected to each other, and they may be connected wirelessly, for example.

Third Example

Figure 5:
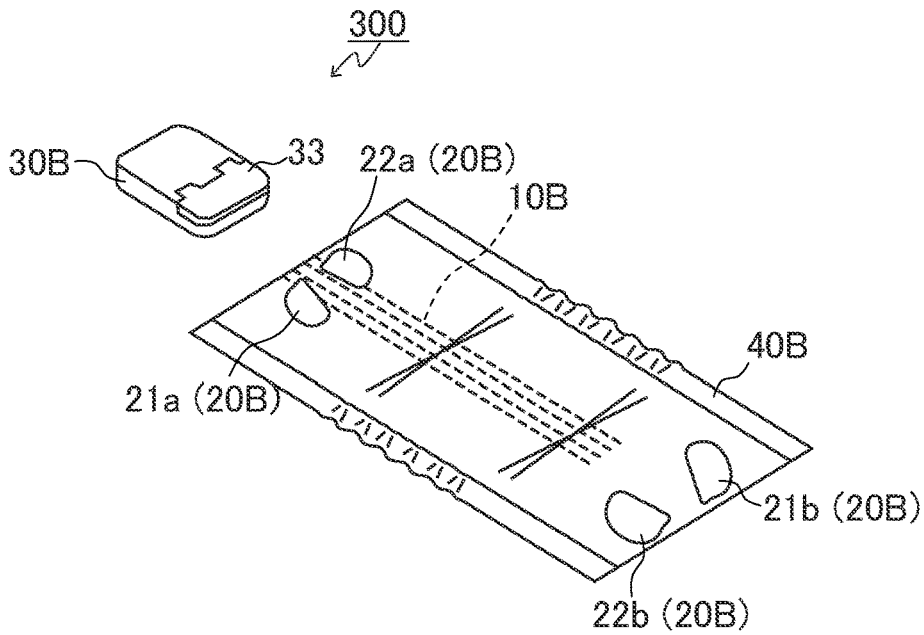
FIG. 5 schematically shows a urinary incontinence treatment device according to a third example.

FIG. 5 schematically shows a urinary incontinence treatment device according to a third example. The urinary incontinence treatment device 300 of example is connectable to a diaper when a diaper 40B provided with a sensor 10B for detecting urination and stimulation pads 20B is used as the diaper, and includes a mechanical member 30B.

In the urinary incontinence treatment device 300, the mechanical member 30B includes a stimulus generation unit 31 and a control unit 32, and further includes a sensor element connecting part 33 connecting the sensor 10B to the mechanical member 30B. The mechanical member 30B is the same as the mechanical member 30 in the first example except that it further includes the sensor element connecting part 33.

The sensor 10B provided in the diaper 40B is connected to the sensor element connecting part 33 of the mechanical member 30B, whereby it is electrically connected to the control unit 32 included in the mechanical member 30B. When the sensor 10B detects urination, the detection of urination is transmitted to the control unit 32 via the sensor element connecting part 33. The control unit 32 and the stimulus generation unit 31 are electrically connected to each other. The stimulus generation unit 31 generates signals for causing the stimulation pads 20B to apply a stimulus to the wearer. The control unit 32 controls the stimulus generation unit 31 to generate the signal in response to urination detection by the sensor 10B.

The sensor 10B shown in FIG. 5 includes a pair of strip-shaped conductors, and one end of each conductor extends to an end of the diaper 40B. The sensor 10B can detect urination based on the difference in electrical property between when urine (water) is not present and when urine (water) is present in a region between these conductors. The sensor element connecting part 33 has a clip-like shape, and can hold the one ends of the conductors together with the diaper 40B. In this manner, the sensor element connecting part 33 connects the sensor 10B to the mechanical member 30B.

Although the stimulation pads 20 and the mechanical member 30 are connected wirelessly in FIG. 5, they may be connected with each other via a cable or the like as shown in FIGS. 1 and 4. In this example, by attaching the mechanical member 30B (reusable) to the disposable diaper 40B provided with the sensor 10B and the stimulation pads 20B, the daily use of the urinary incontinence treatment device is further simplified. The sensor 10B and the stimulation pads 20B can be formed directly on a diaper and provided with device functionality by patterning a conductive material such as a conductive resin. The patterning can be achieved by, for example, printing, transferring, drawing, and plating. By forming the sensor and the stimulation pads in this manner, these members can be made lighter and thinner. This reduces the physical irritation when the diaper is worn, whereby a sense of discomfort is eliminated. In addition, downward slippage of the diaper caused by the self-weight is reduced, thus allowing more stable fit of the diaper. Regarding the elimination of a sense of discomfort, less unpleasant sensation especially while the wearer is sleeping is desirable in terms of allowing the wearer to have a good sleep. Moreover, the manufacturing process of the treatment device is simplified, which is expected to lead to cost reduction and broader utility.

Examples of Use

There are two types of pathological conditions relating to the bladder sensation. A normal urge to urinate (stretch stimulus) when the bladder is stretched (when the bladder is full of urine) is responded by the myelinated nerves. Thus, in a pathological condition in which there is some disorder in the nerves responding to normal urges to urinate such as when an urge to urinate (stretch stimulus) is perceived somewhat earlier, stimulation at a frequency of 200 Hz to 300 Hz, which is centered on 250 Hz, works effectively. On the other hand, pathological urges to urinate (noxious stimulus, stimulus leading to pain) caused by diseases such as cystitis due to bacterial infection are responded by the unmyelinated nerves. Thus, stimulation at a frequency of 1 Hz to 10 Hz, which is centered on 5 Hz, works effectively.

In conventional low-frequency treatments, it is necessary to apply a stimulus for about 20 minutes to 1 hour. In contrast, our urinary incontinence treatment device enables "neuromodulation" by directly stimulating the target nerves, and it is thus expected that stimulation at a frequency of 200 Hz to 300 Hz and stimulation at a frequency of 1 Hz to 10 Hz both bring about therapeutic effects in a short time (e.g., 1 second to 5 minutes). Moreover, it is likely that abnormal nerves (nerves that require treatment) can be treated selectively, whereby adverse effects on other surrounding normal nerves can be avoided. Some myelinated nerves respond to stimulation at around 2,000 Hz. We use electrical signals having a frequency of 4,000 Hz to 4,300 Hz, and this is also preferable from the viewpoint of not affecting the myelinated nerves that respond to stimulation at a frequency of around 2,000 Hz.

After the occurrence of urinary incontinence, the urinary incontinence treatment device applies, upon urination detection by the sensor, electrical stimuli to the patient (wearer) from the stimulation pads. The electrical stimulation either at a frequency of around 250 Hz or at a frequency of around 5 Hz may be applied according to the pathological condition. Alternatively, when there are a plurality of causes or the cause is unknown, stimulation at 250 Hz may be applied for a predetermined period of time (e.g., from 1 to 60 seconds), and thereafter, stimulation at 5 Hz may be applied for a predetermined period of time (e.g., from 1 to 60 seconds). In stimulation at a frequency of 250 Hz, for example, the frequency of the electrical signal supplied to the first pair of stimulation pads is set to 4,000 Hz and the frequency of the electrical signal supplied to the second pair of stimulation pads is set to 4,250 Hz and these two electrical signals with different frequencies are delivered such that they intersect each other in the body, whereby a low-frequency stimulus of 250 Hz generated due to the phase difference between them can be applied to a portion where these electrical signals intersect each other in the body. In stimulation at a frequency of 5 Hz, for example, the frequency of the electrical signal supplied to the first pair of stimulation pads is set to 4,000 Hz and the frequency of the electrical signal supplied to the second pair of stimulation pads is set to 4,005 Hz and these two electrical signals with different frequencies are delivered such that they intersect each other in the body, whereby a low-frequency stimulus of 5 Hz generated due to the phase difference between them can be applied to a portion where these electrical signals intersect each other in the body.

Urinary incontinence caused by involuntary contraction of the bladder occurs owing to abnormal firing of the sensory nerves in the overactive bladder and the neurogenic bladder. Of the sensory nerve fibers of the bladder, Aδ-fibers are responsive to hyperextension of the bladder wall, and C-fibers are responsive to noxious stimuli. Thus, a tailor-made treatment for a patient-specific cause of urinary incontinence becomes possible by specifying the frequency used for treatment according to the pathological condition of the patient. For example, even when patients will receive a treatment for the same period of time (e.g., 10 minutes) from the moment when the symptom of urinary incontinence occurs, it is possible to provide a more effective treatment for each patent by applying stimuli with different frequencies to the patient at a time ratio according to the cause and the degree of the pathological condition of the patient (e.g., a patient A is subjected to stimulation at 5 Hz for 5 minutes and stimulation at 250 Hz for 5 minutes, whereas a patient B is subjected to stimulation at 5 Hz for 2 minutes and stimulation at 250 Hz for 8 minutes).

The time periods for applying the stimuli with the respective frequencies and the balance between the time periods for applying the two frequencies (the ratio and the pattern for applying the frequencies) may be adjusted according to which of the nerves around the bladder need to be specifically stimulated. The time periods for applying the respective frequencies can be controlled by, for example, providing a time input means such as a timer, in the control unit 32, as described above.

The above description illustrates when stimulation is applied using the frequencies of 250 Hz and 5 Hz in combination. However, the frequencies at which the nerve fibers are specifically stimulated vary depending on the diameter of the nerve fibers and the length and the spacing of the myelin sheaths, and thus vary among individuals, albeit they are around 250 Hz and 5 Hz. On this account, it is more effective to perform a treatment using the urinary incontinence treatment device after measuring the desired frequencies for each patient. In bladder perception, frequencies that work specifically to the nerves requiring a treatment with stimulation can be clarified by performing a nerve fiber selective sensory function test on the lower urinary tract using a peripheral nerve perception threshold measurement device for urinary function testing such as Neurometer®.

Specifically, in the following pathological conditions, it is well known that urinary incontinence, frequent urination and the like are caused by specific nerve fibers. "Nocturnal enuresis" in infants, toddlers and the like is a capacity-dependent urinary incontinence that occurs when the bladder is overloaded and resolves spontaneously with age. The specific nerve fibers responsible for this are myelinated Aδ-fibers, which are nerve fibers that transmit normal urges to urinate, and the frequency that specifically works for these nerve fibers is 250 Hz, although it varies among individuals as described above. "Urge urinary incontinence" is urinary incontinence caused by spinal cord injury or frontal lobe damage in the elderly, and "intractable nocturnal enuresis" is urinary incontinence caused by an underdeveloped spinal cord or the like. The specific nerve fibers responsible for this are unmyelinated C-fibers, which are nerve fibers that transmit pathological urges to urinate, pain and the like, and the frequency that specifically works for these nerve fibers is 5 Hz, although it varies among individuals as described above. Thus, in the following example, whether low-frequency treatments using the frequencies specific to these nerve fibers can treat the pathological conditions was examined using experimental animals (mice).

Examples

Animal Experiment

An animal experiment was performed using mice. The details of the animals used in the experiment are as follows:
Animal species: mouse
Sex: female
Number of animals used: 8 (four overactive bladder mice and four normal mice (control)).
Overactive Bladder Mice Overactive bladder mice were selected as experimental animals to reproduce pathologically frequent urination. In overactive bladder mice, unmyelinated C-fibers are mainly responsible for bladder perception, whereas in normal mice, myelinated Aδ-fibers are mainly responsible for bladder perception. The overactive bladder mice were prepared in advance by injecting 1.5% $H_2O_2$ physiological saline into the bladders of normal mice using an urethral catheter and draining the fluid from the bladders 30 minutes later.
Implantation of Electrode Pads The mice were subcutaneously implanted with low-frequency stimulation pads (electrode pads) at four locations shown in FIG. 3 under general anesthesia. The electrode pads were 8 mm in diameter, as a specification for use in mice. The urinary incontinence treatment device, which uses stimulation pads (electrode pads) configured to be placed in contact with the body surface or adhered to the body surface, is characterized in that it does not require any surgical procedure and thus is minimally invasive. However, in the animal experiment, the electrode pads were subcutaneously implanted because it was difficult to reproduce a clothed condition and also to provide constant experimental conditions.

Urinary Incontinence Treatment Experiment (Interference Low-Frequency Stimulation Experiment)

The following experiment was performed according to the established animal experimental method on urinary function.

Under general anesthesia, each mouse was subjected to catheterization via the apex of the bladder. Thereafter, physiological saline was injected (6 mL/hour) to the bladder of each mouse in an awake state via the catheter to store urine in the bladder at a constant rate, and urination from the urethra was observed. At this time, the mouse was fixed prone.

For the overactive bladder mice and the normal mice, changes in the amount of urine excreted in one urination before and after being subjected to low-frequency (5 Hz and 250 Hz) stimulation (treatment) in an awake state were observed. For stimulation at a frequency of 5 Hz, the frequency of the electrical signal supplied to the first pair of stimulation pads was set to 4,000 Hz and the frequency of the electrical signal supplied to the second pair of stimulation pads was set to 4,005 Hz, whereby a low-frequency stimulus of 5 Hz generated due to the phase difference between them was applied to a portion where the electrical signals intersected with each other in the body. For stimulation at a frequency of 250 Hz, the frequency of the electrical signal supplied to the first pair of stimulation pads was set to 4,000 Hz and the frequency of the electrical signal supplied to the second pair of stimulation pads was set to 4,250 Hz, whereby a low-frequency stimulus of 250 Hz generated due to the phase difference between them was applied to a portion where these electrical signals intersected with each other in the body. The experiment was performed in the following manner, using two overactive bladder mice and two normal mice in an awake state for each stimulation frequency:

(1) The amount of urine excreted in one urination was measured before low-frequency stimulation.

(2) At the moment when urination was observed, the mice were subjected to low-frequency stimulation for 1 minute. This operation was performed for three times of urination.

(3) The amount of urine excreted in one urination was measured after the low-frequency stimulation.

Observation of each urination was performed when the mice were in an awake state, and a plurality of persons visually observed the urinations. The excreted urine was collected in a urine collection tray, and the amount of urine was measured using a measuring instrument. Table 1 shows the results obtained when the stimulus frequency was 5 Hz, and Table 2 shows the results obtained when the stimulus frequency was 250 Hz. The "OAB" in these tables stands for overactive bladder mice.

TABLE 1

| Mice | Amount of urine excreted in one urination (mL) | | Increase ratio of amount of urine |
| | Before stimulation | After stimulation | excreted in one urination (%) |
| --- | --- | --- | --- |
| Normal 1 | 0.38 | 0.316 | 83 |
| Normal 2 | 0.114 | 0.105 | 92 |
| OAB 1 | 0.073 | 0.164 | 225 |
| OAB 2 | 0.089 | 0.186 | 210 |

TABLE 2

| Mice | Amount of urine excreted in one urination (mL) | | Increase ratio of amount of urine excreted in one urination (%) |
|---|---|---|---|
| | Before stimulation | After stimulation | |
| Normal 1 | 0.112 | 0.266 | 236 |
| Normal 2 | 0.077 | 0.176 | 228 |
| OAB 1 | 0.18 | 0.176 | 96 |
| OAB 2 | 0.117 | 0.163 | 138 |

As can be seen from Table 1 (OAB 1 and OAB 2), in the overactive bladder mice, the stimulation at 5 Hz increased the amount of urine excreted in one urination to more than twice. Since the overactive bladder mice were in a pathological condition of frequent urination, stimulation at 5 Hz, which is a frequency specific to the unmyelinated C-fibers, was expected to be effective in treating the pathological condition, and it was confirmed that the results obtained were as desired. In contrast, as can be seen from Table 2 (OAB 1 and OAB 2), the stimulation at 250 Hz did not cause any marked change in the overactive bladder mice. This reveals, since the overactive bladder mice did not have a pathological condition of capacity-dependent incontinence, stimulation at 250 Hz, which is a frequency specific to the myelinated A$\delta$-fibers, did not bring about any therapeutic effect.

On the other hand, the stimulation at 5 Hz did not cause any marked change in the normal mice as can be seen from Table 1 (Normal 1 and Normal 2), whereas the stimulation at 250 Hz increased the amount of urine excreted in one urination to more than twice as can be seen from Table 2 (Normal 1 and Normal 2). The normal mice were used in the experiment as a model of nocturnal enuresis caused by a small amount of urine excreted in one urination, and the stimulation at 250 Hz, which is the frequency specific to the myelinated A$\delta$-fibers, effectively increased the amount of urine excreted in one urination. On the other hand, we found that, since the normal mice did not have pathological urges to urinate or pain, the stimulation at 5 Hz, which is a frequency specific to the unmyelinated C-fibers, did not bring about any therapeutic effect.

The above example (animal experiment) confirmed that the amount of urine excreted in one urination is increased by applying low-frequency stimulus at a frequency suitable for the nerve fibers specific to the pathological condition at the moment when urination (urinary incontinence) occurred. The above example demonstrates that a more effective tailor-made treatment is possible by applying a low-frequency stimulus with a patient-specific frequency at a patient-specific timing (when urinary incontinence occurs) in consideration of the pathological condition of each individual patient.

We provide urinary incontinence treatment devices that use the stimulation pads (electrode pads) configured to be placed in contact with the body surface or adhered to the body surface and thus can be expected to bring about stable therapeutic effects by effectively stimulating the nerves that are deep inside the body and localized around the bladder, even though the device does not require any surgical procedure and thus is minimally invasive. The urinary incontinence treatment device can be, for example, a diaper-type treatment device, which allows a patient to have a treatment merely by wearing the treatment device. Accordingly, it requires little assistance from a family member who takes care of the patient or a caregiver, thus allowing the burden on the caregiver and the like to be extremely small. Moreover, the urinary incontinence treatment device can stimulate nerve fibers localized around the bladder at nerve fiber-specific frequencies according to the pathological conditions and thus can realize tailor-made treatments for patients according to their pathological conditions of urinary incontinence.

The invention claimed is:

1. A urinary incontinence treatment device comprising:
a sensor that detects urination;
stimulation pads configured to apply a stimulus to a wearer; and
a mechanical member including:
(i) a stimulus generator that generates a signal causing the stimulation pads to apply the stimulus to the wearer; and
(ii) a controller that controls the stimulus generator to generate the signal in response to urination detection by the sensor,
wherein
the stimulation pads include a first pair of stimulation pads and a second pair of stimulation pads,
the stimulus generator supplies electrical signals having different frequencies to the first pair of stimulation pads and the second pair of stimulation pads, respectively,
the first pair of stimulation pads and the second pair of stimulation pads are each a pair of electrode pads configured to apply an electrical stimulus to the wearer when being supplied with the electrical signal,
the frequencies of the electrical signals are set to 4,000 Hz to 4,300 Hz and a difference between the frequency set for the first pair of stimulation pads and the frequency set for the second pair of stimulation pads is 200 Hz to 300 Hz centered on 250 Hz, which is a frequency that specifically stimulates myelinated A$\delta$-fibers and 1 Hz to 10 Hz centered on 5 Hz, which is a frequency that specifically stimulates unmyelinated C-fibers,
the first pair of stimulation pads and the second pair of stimulation pads are arranged such that the electrical signal applied from the first pair of stimulation pads and the electrical signal applied from the second pair of stimulation pads intersect each other in the wearer's body and a resulting interference wave reaches the bladder, and
the controller includes a frequency adjustment section that sets the frequencies according to which of the myelinated Ad-fibers or the unmyelinated C-fibers are responsible for a pathological condition to be treated.

2. The urinary incontinence treatment device according to claim 1, wherein the sensor, the stimulation pads, and the mechanical member are attachable to a diaper.

3. The urinary incontinence treatment device according to claim 1, further comprising a diaper, wherein the sensor and the stimulation pads are provided in the diaper, and the mechanical member is connected to the sensor and the stimulation pads.

4. The urinary incontinence treatment device according to claim 3, wherein at least one of the sensor or the stimulation pads are formed on the diaper by patterning a conductive material.

5. A urinary incontinence treatment device attachable to a diaper that includes a sensor that detects urination, the device comprising:
stimulation pads configured to apply a stimulus to a wearer; and
a mechanical member including:

(i) a stimulus generator that generates a signal causing the stimulation pads to apply the stimulus to the wearer;

(ii) a sensor element connecting part that connects the sensor to the mechanical member; and (iii) a controller connected to the sensor element connecting part controls the stimulus generator to generate the signal in response to urination detection by the sensor, wherein the stimulation pads include a first pair of stimulation pads and a second pair of stimulation pads, the stimulus generation unit supplies electrical signals having different frequencies to the first pair of stimulation pads and the second pair of stimulation pads, respectively, the first pair of stimulation pads and the second pair of stimulation pads are each a pair of electrode pads configured to apply an electrical stimulus to the wearer when being supplied with the electrical signal, the frequencies of the electrical signals are set to 4,000 Hz to 4,300 Hz and a difference between the frequency set for the first pair of stimulation pads and the frequency set for the second pair of stimulation pads is 200 Hz to 300 Hz centered on 250 Hz, which is a frequency that specifically stimulates myelinated Aδ-fibers and 1 Hz to 10 Hz centered on 5 Hz, which is a frequency that specifically stimulates unmyelinated C-fibers, the first pair of stimulation pads and the second pair of stimulation pads are arranged such that the electrical signal applied from the first pair of stimulation pads and the electrical signal applied from the second pair of stimulation pads intersect each other in the wearer's body and a resulting interference wave reaches the bladder, and the controller includes a frequency adjustment section that sets the frequencies according to which of the myelinated Ad-fibers or the unmyelinated C-fibers are responsible for a pathological condition to be treated.

6. The urinary incontinence treatment device according to claim 5, wherein at least one of the sensor or the stimulation pads are formed on the diaper by patterning a conductive material.

7. A urinary incontinence treatment device connectable to a diaper that includes a sensor that detects urination and stimulation pads configured to apply a stimulus to a wearer, the stimulation pads being electrode pads configured to apply an electrical stimulus to the wearer when being supplied with an electrical signal and including a first pair of stimulation pads and a second pair of stimulation pads, and the first pair of stimulation pads and the second pair of stimulation pads being arranged such that an electrical signal applied from the first pair of stimulation pads and an electrical signal applied from the second pair of stimulation pads when the diaper is worn intersect each other in the wearer's body and a resulting interference wave reaches the bladder, the urinary incontinence treatment device comprising:

a mechanical member including:

(i) a stimulus generator that generates a signal causing the stimulation pads to apply the stimulus to the wearer;

(ii) a sensor element connecting part that connects the sensor to the mechanical member; and (iii) a controller connected to the sensor element connecting part controls the stimulus generator to generate the signal in response to urination detection by the sensor, wherein the stimulus generator supplies electrical signals having different frequencies to the first pair of stimulation pads and the second pair of stimulation pads, respectively, the frequencies of the electrical signals are set to 4,000 Hz to 4,300 Hz and a difference between the frequency set for the first pair of stimulation pads and the frequency set for the second pair of stimulation pads is 200 Hz to 300 Hz centered on 250 Hz, which is a frequency that specifically stimulates myelinated Aδ-fibers and 1 Hz to 10 Hz centered on 5 Hz, which is a frequency that specifically stimulates unmyelinated C-fibers, and the controller includes a frequency adjustment section that sets the frequencies according to which of the myelinated Aδ-fibers or the unmyelinated C-fibers are responsible for a pathological condition to be treated.

8. The urinary incontinence treatment device according to claim 7, wherein at least one of the sensor or the stimulation pads are formed on the diaper by patterning a conductive material.

9. The urinary incontinence treatment device according to claim 1, wherein the controller includes a time adjustment section that sets a stimulus application time according to a pathological condition.

10. The urinary incontinence treatment device according to claim 1, wherein the controller includes a frequency adjustment section and a time adjustment section, that set a frequency and a stimulus application time, respectively, according to a pathological condition.

* * * * *